United States Patent
Anraku et al.

(12)
(10) Patent No.: US 6,821,785 B1
(45) Date of Patent: Nov. 23, 2004

(54) VACUUM SAMPLE COLLECTING TUBE AND METHOD OF COLLECTING SAMPLE UNDER VACUUM

(75) Inventors: Hideo Anraku, Shinnanyo (JP); Ryusuke Okamoto, Shinnanyo (JP)

(73) Assignee: Sekisui Chemical Co., Ltd., Osaka (JP)

( * ) Notice: Subject to any disclaimer, the term of this patent is extended or adjusted under 35 U.S.C. 154(b) by 0 days.

(21) Appl. No.: 10/009,683

(22) PCT Filed: Jun. 16, 1999

(86) PCT No.: PCT/JP99/03195
§ 371 (c)(1),
(2), (4) Date: Feb. 22, 2002

(87) PCT Pub. No.: WO00/76401
PCT Pub. Date: Dec. 21, 2000

(51) Int. Cl.[7] .................................................. A61M 5/32
(52) U.S. Cl. ......................... 436/66; 422/100; 422/102; 604/232; 604/403; 604/412
(58) Field of Search ............................. 422/58, 61, 99, 422/100, 102; 436/66–71, 11; 604/232, 403, 412

(56) References Cited

U.S. PATENT DOCUMENTS

| 4,434,235 A | * | 2/1984 | Rabi et al. .................. 436/110 |
| 4,876,068 A | * | 10/1989 | Castaneda ..................... 422/58 |
| 4,917,867 A | * | 4/1990 | Jensen et al. ............... 422/102 |

FOREIGN PATENT DOCUMENTS

| JP | 8-289881 | 5/1996 |
| JP | 11-235329 | 8/1999 |

* cited by examiner

Primary Examiner—Lyle A. Alexander
(74) Attorney, Agent, or Firm—Sughrue Mion, PLLC

(57) ABSTRACT

The present invention has for its object to provide a vacuum sampling tube which is capable of preventing a pretreating reagent accommodated in the vacuum sampling tube from entering the blood vessel and the like even in the event of a backflow of a specimen, such as blood, during vacuum sampling, such as vacuum blood collecting, and a vacuum sampling method.

8 Claims, 12 Drawing Sheets

VACUUM SAMPLE COLLECTING TUBE AND METHOD OF COLLECTING SAMPLE UNDER VACUUM

TECHNICAL FIELD

The present invention relates to a vacuum sampling tube to be used in the so-called vacuum sampling system for collection of specimens which are aspiratable by utilizing a pressure difference between the inside and outside of the tube and a vacuum sampling method using said vacuum sampling tube. Above all else, the invention relates to a vacuum blood collecting tube for use in clinical examinations to be performed on blood specimens and a vacuum blood collecting method using said blood collecting tube.

BACKGROUND ART

While a typical vacuum blood collecting system is described in Japanese Kokai Publication Sho-62-227316, the fundamental construction of the system comprises:

1) as illustrated in FIG. 12, a vacuum blood collecting tube 30 comprising a bottomed tubular casing 32 and a plug 31 having needle hole-sealable, gas-barrier properties as sealing the open end of said casing gas-tight to thereby keep a negative pressure within said casing;
2) as illustrated in FIG. 13, a vacuum blood collecting needle 40 comprising a hollow needle of metal having needle tips 41 and 42 at both ends and a hub 43 provided with a male thread 44 on the plug-piercing side; and
3) as illustrated in FIG. 14, a holder for vacuum blood collection 50 having a blood collecting needle-retaining aperture 51 provided with a female thread engageable with the male thread of said hub 43 so that said vacuum blood collecting tube 30 may be accepted into an internal cavity 52.

In blood collecting, the vacuum blood collecting needle 40 is threaded onto the blood collecting needle-retaining aperture 51 of the holder for vacuum blood collection 50. Then, the vacuum blood collecting tube 30 is inserted into said holder 50 and forced against the needle tip 42 of the vacuum blood collecting needle 40 to the extent that the plug 31 is not completely pierced through so as to temporarily seal the needle tip 42. This is done to prevent the blood from leaking out of the needle tip 42 when the needle tip 41 is inserted into a blood vessel.

The person in charge of blood collection holds the whole of said blood collecting needle/said holder/said blood collecting tube assembly by hand in an incumbent position along the axis of the subject's blood vessel and sticks the needle tip 41 on the blood vessel piercing side into the blood vessel. Then, as he or she advances said blood collecting tube 30 farther into said holder 50, the needle tip 42 on the plug piercing side penetrates through the plug 31, with the result that the blood flows into said blood collecting tube due to the pressure difference between the blood collecting tube side and the blood vessel side. Then, as the pressure difference is abolished, the blood inflow stops. Therefore, the whole assembly is withdrawn from the blood vessel to complete a blood collecting work.

Usually, depending on the object of an examination, said blood collecting tube involves a coagulation accelerator, an anticoagulant, a deproteinizing agent, a blood component stabilizer, and/or the like for the pretreatment of a blood specimen in its inside. However, since these drugs denature the blood into a nonphysiological state different from its state in vivo, the risk of these chemicals finding their way into the subject's body in the event of a backflow by mistake during blood collecting has been pointed out.

For the prevention of such a backflow, Japanese Kokai Publication Sho-49-51784 and Japanese Kokai Publication Sho-50-12892 each proposes a vacuum blood collecting needle provided with an elastic backflow prevention valve and Japanese Kokai Publication Sho-54-4191 proposes a vacuum blood collecting tube plug which is provided with a similar elastic backflow prevention valve. The underlying principle of these proposals is that as long as a pressure difference exists between the blood vessel side and the blood collecting tube side, the elastic valve is forced open by the hurriedly incoming blood flow, thus allowing blood collection, but as the pressure difference is abolished, the valve closes to arrest the backflow. However, partly because of the inevitably complicated structures of the blood collecting needle and plug and partly because said pressure difference is inherently small when the blood collecting size setting is small relative to the capacity of the blood collecting tube, the variation in the actual blood collecting size becomes remarkable when a variation occurs in the opening or closing force of the elastic valve.

SUMMARY OF THE INVENTION

The present invention, developed to overcome the above-mentioned disadvantages, has for its object to provide a vacuum sampling tube which is capable of preventing a pretreating reagent accommodated in the vacuum sampling tube from entering the blood vessel and the like even in the event of a backflow of a specimen, such as blood, during vacuum sampling, such as vacuum blood collecting, and a vacuum sampling method using said vacuum sampling tube.

A vacuum sampling tube according to the first aspect of the present invention is a sampling vessel comprising
two tubular casings differing in size and each having a closed bottom and an opening at the other end as assembled together in the manner of a nest of boxes, wherein
1) the inner casing of the nest of boxes is sealed gas-tight at its open end by a gas-barrier, needle hole-sealable plug, whereby a negative pressure state is kept within said casing,
2) the outer casing of the nest of boxes is substantially not in contact with an outer bottom surface of said inner casing of the nest of boxes but is detachably associated at the open end of said outer casing with an outer peripheral surface of said inner casing in the vicinity of its open end in substantially liquid-tight relation, and
3) a specimen-pretreating reagent is accommodated in a space between said inner casing and said outer casing.

A vacuum sampling tube according to the second aspect of the invention is a sampling vessel comprising
a tubular casing having a closed bottom and an opening at the other end and
a cylinder having openings at both ends as assembled in said casing in the manner of a nest of boxes, wherein
1) the open top end of the inner cylinder of the nest of boxes is sealed gas-tight by a gas-barrier, needle hole-sealable plug,
2) said cylinder is detachably associated, respectively, with the open end of said tubular casing in the vicinity of its open top end in substantially liquid-tight relation and with a plug means of said tubular casing in the vicinity of cylinder's open bottom end in substantially gas-tight relation, 3) a negative pressure state is kept with in said cylinder, and 4) a specimen-pretreating reagent is accommodated in a space between said cylinder and said tubular casing.

A vacuum sampling tube according to the third aspect of the invention is a sampling vessel comprising a tubular casing having a closed bottom and an opening at the other end and a cylinder having openings at both ends as assembled in said casing in the manner of a nest of boxes, wherein 1) the open top end of the inner cylinder of the nest of boxes is sealed gas-tight by a gas-barrier, needle hole-sealable plug, 2) said cylinder is detachably associated, respectively, with the open end of said tubular casing in the vicinity of its open top end in substantially liquid-tight relation and with a plug means of said tubular casing in the vicinity of cylinder's open bottom end in substantially gas-tight relation, 3) said open bottom end of the cylinder and said plug means of the tubular casing are provided with complementary notches and, by bringing said cylinder into sliding rotation about its axis, internal spaces of said cylinder and said casing are reversibly brought into communication or out of communication, 4) a negative pressure state is kept within said cylinder, and 5) a specimen-pretreating reagent is accommodated in a space between outer surface of said cylinder and inner surface of said casing.

A vacuum sampling tube according to the fourth aspect of the invention is a sampling vessel comprising a tubular casing having a closed bottom and an opening at the other end and a cylinder having openings at both ends as assembled in said casing in the manner of a nest of boxes, wherein 1) the open top end of the inner cylinder of the nest of boxes is sealed gas-tight by a gas-barrier, needle hole-sealable plug while the open bottom end thereof is sealed gas-tight by a gas-barrier member which can be broken through at least locally, whereby a negative pressure state is kept within said cylinder, 2) said cylinder is designed in such manner that its open bottom end faces a plunger member disposed inwardly of the closed bottom end of said tubular casing, and is detachably and slidably associated with the open end of said tubular casing in substantially liquid-tight relation in the vicinity of its open top end, and 3) a specimen-pretreating reagent is accommodated in a space between outer surface of said cylinder and inner surface of said tubular casing.

A vacuum sampling method according to the fifth aspect of the invention comprises using the vacuum sampling tube according to the first aspect of the invention and collecting a specimen by vacuum into said inner casing followed by causing said inner casing to be dissociated from said outer casing, and adding the specimen in said inner casing to a pretreating reagent in said outer casing.

A vacuum sampling method according to the sixth aspect of the invention comprises using the vacuum sampling tube according to the second aspect of the invention and collecting a specimen by vacuum into said cylinder followed by causing said cylinder and said tubular casing to slide axially to dissociate the open bottom end of said cylinder from said plug means, thereby introducing the specimen in said cylinder into a pretreating reagent in said tubular casing.

The vacuum sampling method according to the seventh aspect of the invention comprises using the vacuum sampling tube according to the third aspect of the invention and collecting a specimen by vacuum into said cylinder followed by bringing said cylinder and said tubular casing into relative rotation about the axis to substantially align the notch of the open bottom end of said cylinder with the notch of said plug means, thereby bringing internal spaces of said cylinder and said casing into communication and introducing the specimen in said cylinder into a pretreating reagent in said casing.

A vacuum sampling method according to the eighth aspect of the invention comprises using the vacuum sampling tube according to the fourth aspect of the invention and collecting a specimen by vacuum into said cylinder followed by pushing said cylinder into said tubular casing to break the breakable member at the bottom end of said cylinder by the plunger member of said tubular casing, thereby bringing both internal spaces of said cylinder and said casing into communication and introducing the specimen in said cylinder into a pretreating reagent in said casing.

According to any of the vacuum sampling tubes according to the first through fourth aspects of the invention, since the pretreating reagent which would otherwise find its way into the subject's body in the event of a backflow is accommodated in a vessel independent of the direct vessel for a vacuum sampling, the risk in the event of a backflow of blood or the like during sampling such as blood collecting can be obviated.

According to any of the vacuum sampling methods according to the fifth through eighth aspects of the invention, since the pretreating reagent which would otherwise finds its way into the subject's body in the event of a backflow is accommodated in a vessel independent of the direct vessel for a vacuum sampling, the blending of blood or the like with the pretreating reagent takes place after the vacuum sampling, so that the risk in the event of a backflow of blood or the like during sampling such as blood collecting can be obviated.

Figure 1:
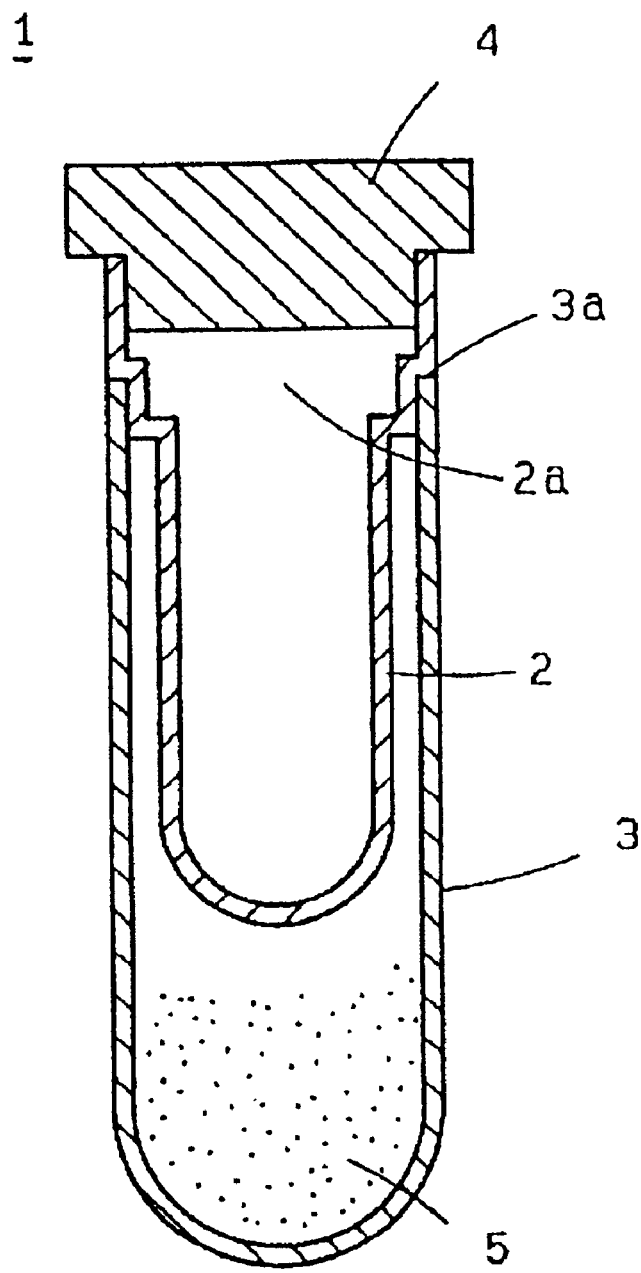
FIG. 1 is a sectional view showing an example of a vacuum sampling tube according to the first aspect of the invention.

On the drawings, the reference numerals 1, 11, 21 and 61 each represents a vacuum sampling tube, 2 represents an inner casing, 2a represents an open end, 3 represents an outer casing, 3a represents an open end, 4, 14, 24 and 64 each represents a plug, 5, 15, 25 and 65 each represents a pretreating reagent, 12 represents a cylinder, 12a represents an open top end, 12b represents an open bottom end, 13 represents a tubular casing, 13a represents an open end, 13b represents a plug means, 22 represents a cylinder, 22a represents an open top end, 22b represents an open bottom end, 22c represents a notch, 23 represents a tubular casing, 23a represents an open end, 23b represents a plug means, 23c represents a notch, 62 represents a cylinder, 62a represents an open top end, 62b represents an open bottom end, 63 represents a tubular casing, 63a represents an open end, 63b represents a bottomed end, 63c represents a plunger member, 66 represents a gas-barrier member which can be broken through at least locally, 66a represents a breakable part, 67 represents a cylindrical element, 68 represents a plug element, and 68a represents a plunger member.

DETAILED DESCRIPTION OF THE INVENTION

An example of a vacuum sampling tube 1 of the first aspect of the invention is now described, referring to FIG. 1. The vacuum sampling tube 1 is a sampling vessel comprising two tubular casings 2 and 3 differing in size and each having a closed bottom and an opening at the other end as assembled together in the manner of a nest of boxes, and comprises the following structure.
Thus,
1) the inner casing 2 of the nest of boxes is sealed gas-tight at its open end 2a by a gas-barrier, needle hole-sealable plug 4, whereby a negative pressure state is kept within said casing 2, 2) the outer casing 3 of the nest of boxes is substantially not in contact with an outer bottom surface of said inner casing of the nest of boxes but is detachably associated at the open end 3a of said outer casing 3 with an outer peripheral surface of said inner casing 2 in the vicinity of its open end 2a in substantially liquid-tight relation, and 3) a specimen-pretreating reagent 5 is accommodated in a space between said inner casing 2 and said outer casing 3.

The vicinity of the open end 2a of the inner casing 2 as referred to above is not necessarily the open end 2a but may be any location insofar as the inner casing 2 and outer casing 3 can be integrated to constitute a sampling tube 1 with the outer casing 3 held substantially liquid-tight before and during sampling.

Figure 2:
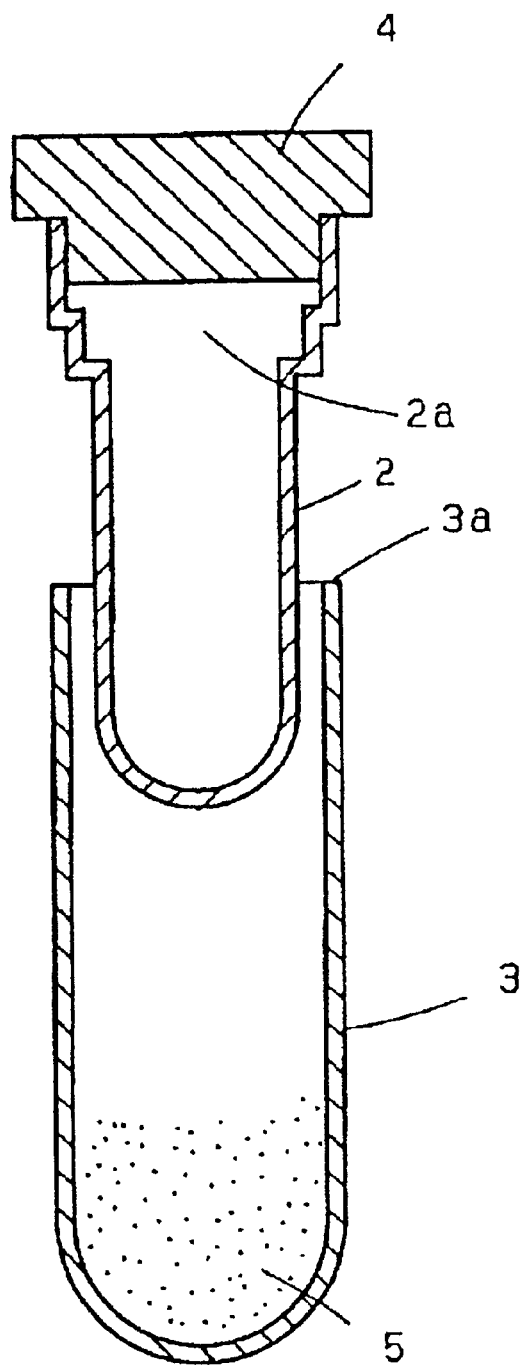
FIG. 2 is a sectional view of the vacuum sampling tube according to the first aspect of the invention, with an inner casing and outer casing in dissociated positions.

The invention in its fifth aspect is concerned with a vacuum sampling method which comprises using the vacuum sampling tube according to the first aspect of the invention and collecting a specimen by vacuum into said inner casing 2 by the routine vacuum sampling method followed by causing said inner casing 2 and said outer casing 3 to be dissociated as illustrated in FIG. 2, removing the plug 4 from said inner casing 2, and adding the specimen in said inner casing 2 to the pretreating reagent in said outer casing 3. Thereafter, both are blended and, assuming that the specimen is blood, it maybe fractionated into blood corpuscles, serum and plasma by the routine method and used in various blood examinations.

Figure 3:
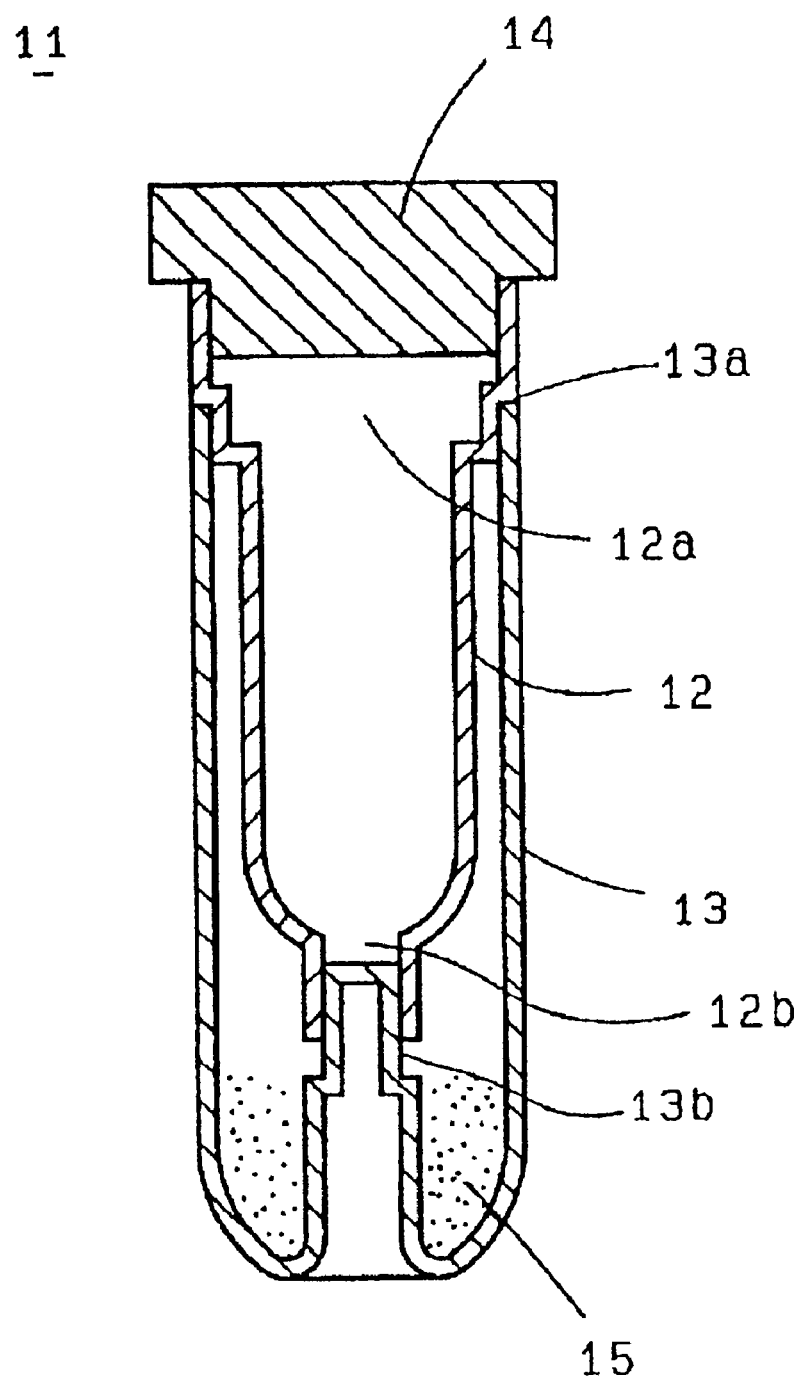
FIG. 3 is a sectional view showing an example of a vacuum sampling tube according to the second aspect of the invention.

An example of a vacuum sampling tube 11 of the second aspect of the invention is now described, referring to FIG. 3. The vacuum sampling tube 11 is a sampling vessel comprising a tubular casing 13 having a closed bottom and an opening at the other end and a cylinder 12 having openings at both ends as assembled in said casing 13 in the manner of a nest of boxes, and comprises the following structure. Thus,
1) the open top end 12a of the inner cylinder 12 of the nest of boxes is sealed gas-tight by a gas-barrier, needle hole-sealable plug 14, 2) said cylinder 12 is detachably associated, respectively, with the open end 13a of said tubular casing 13 in the vicinity of its open top end 12a in substantially liquid-tight relation and with a plug means 13b of said tubular casing 13 in the vicinity of its open bottom end 12b in substantially gas-tight relation, 3) a negative pressure state is kept within said cylinder 12, and 4) a specimen-pretreating reagent 15 is accommodated in a space between said cylinder 12 and said tubular casing 13.

The plug means 13b of said tubular casing 13 is formed in such a manner that the bottom wall surface of said casing 13 is raised inwardly of said casing 13 to form a hollow cylindrical element (however, the top surface of said cylindrical element is closed) and the top end thereof is formed so as to be acceptable within the open bottom end 12b of said cylinder 12 in gas-tight relation. In this embodiment, said plug means 13b and said tubular casing 13 are provided as a one-piece molding.

The vicinity of the open end 12a and the vicinity of the open end 12b, as referred to above, are not necessarily the open end 12a and open end 12b respectively, but may each be any location insofar as the tubular casing 13 and cylinder 12 can be integrated to constitute a sampling tube 11 with the cylinder 12 held substantially liquid-tight and gas-tight before and during sampling.

Figure 4:
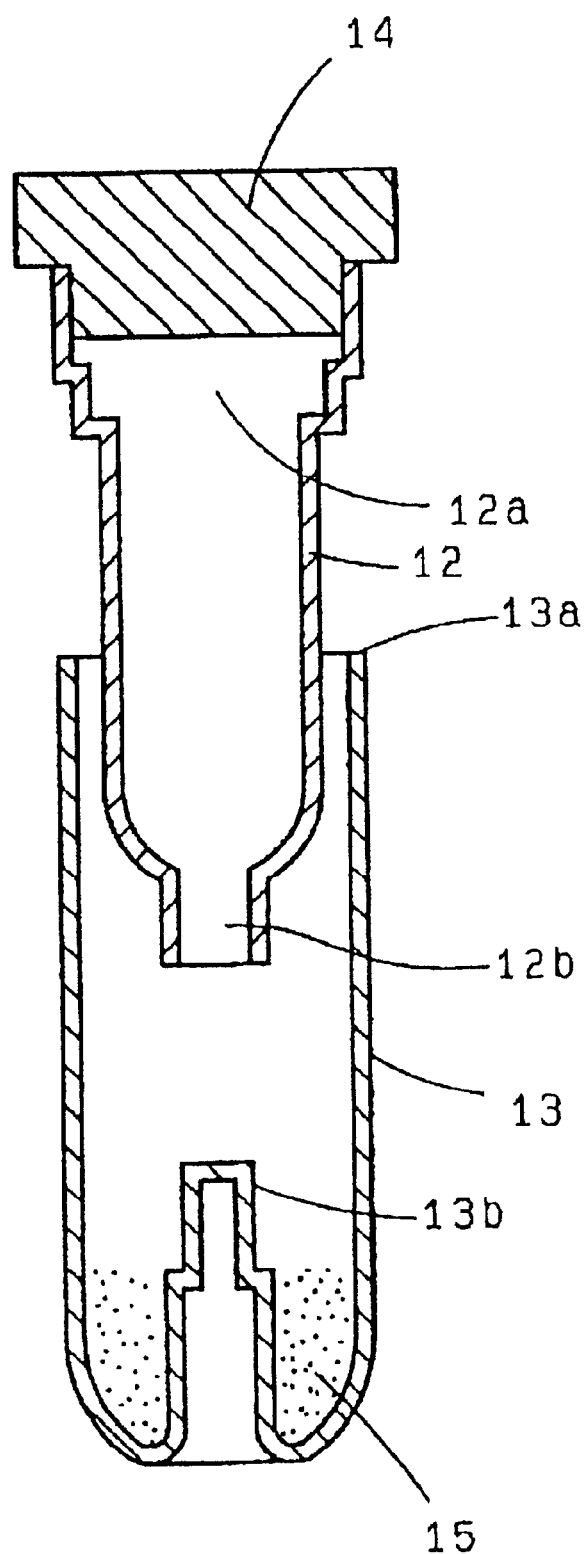
FIG. 4 is a sectional view showing the vacuum sampling tube according to the second aspect of the invention, with a cylinder and tubular casing having been axially slid to dissociate the open bottom end of the cylinder from a plug means of the tubular casing.

The invention in its sixth aspect is concerned with a vacuum sampling method which comprises using the vacuum sampling tube according to the second aspect of the invention, and collecting a specimen by vacuum into said cylinder 12 by the routine vacuum sampling method followed by, as illustrated in FIG. 4, causing said cylinder 12 and said tubular casing 13 to slide axially to dissociate the open bottom end 12b of said cylinder 12 from said plug means 13b, thereby introducing the specimen in said cylinder 12 into the pretreating reagent in said tubular casing 13. Thereafter, both are blended and, assuming that the specimen is blood, it may be fractionated into blood corpuscles, serum and plasma by the routine method and used in various blood examinations.

Figure 5:
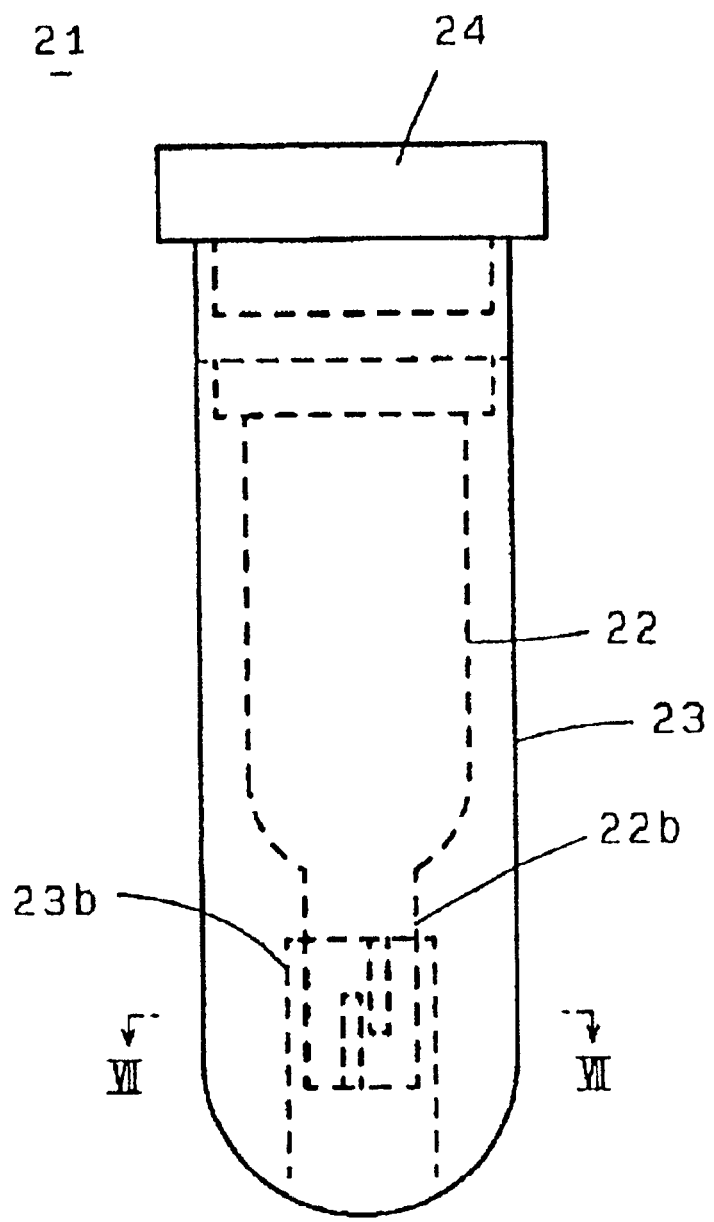
FIG. 5 is a front view of a vacuum sampling tube according to the third aspect of the invention.
Figure 6:
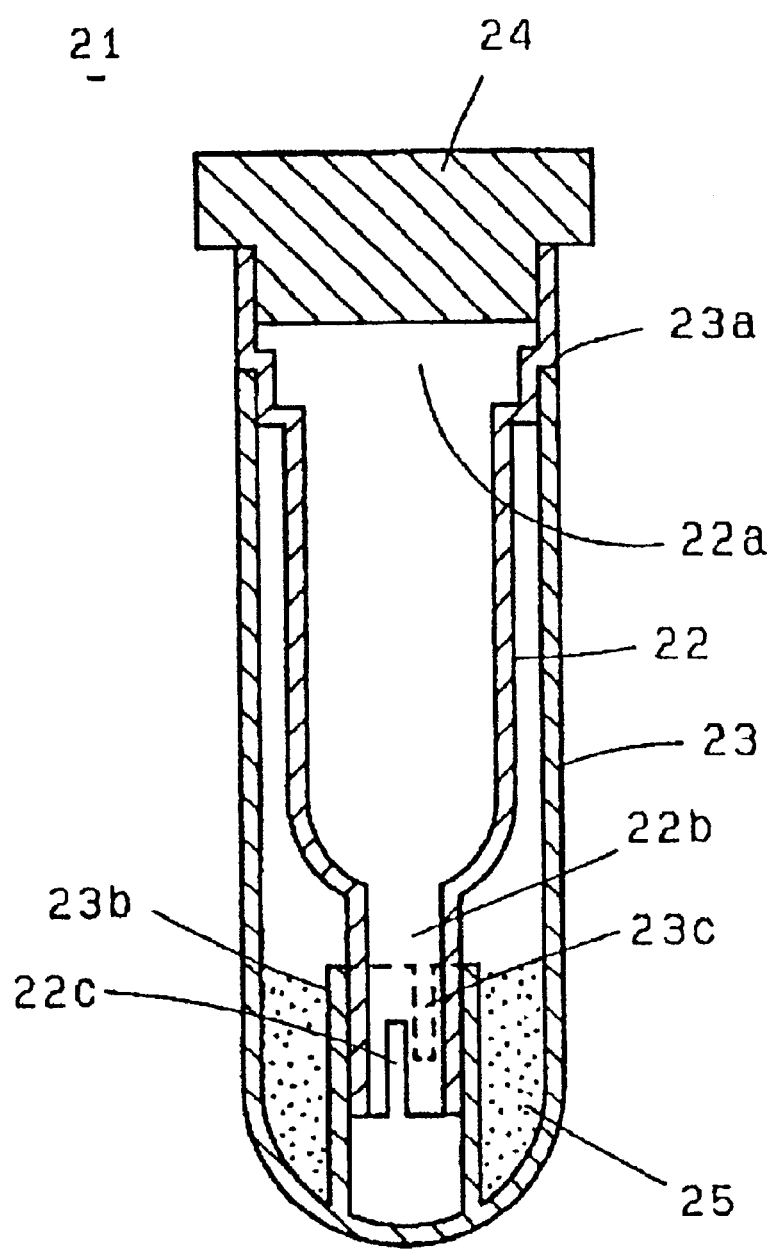
FIG. 6 is a longitudinal section view of FIG. 5.
Figure 7:
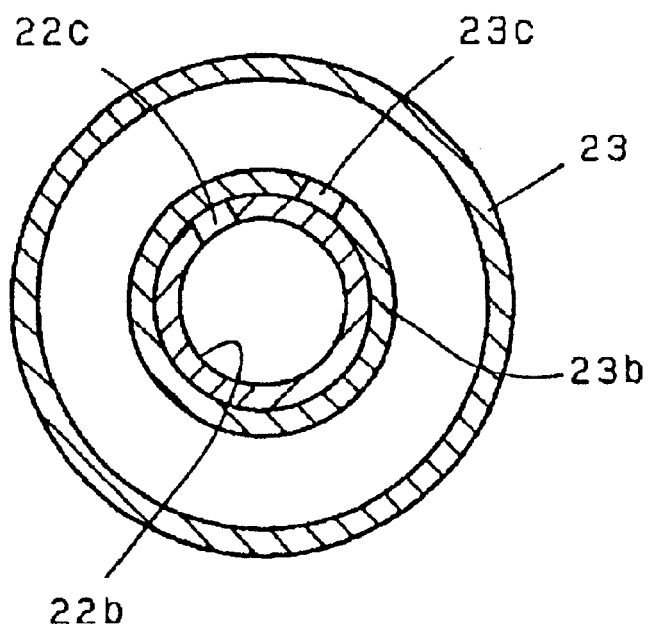
FIG. 7 is a sectional view taken along the line VII—VII of FIG. 5 on magnified scale.

An example of a vacuum sampling tube 21 of the third aspect of the invention is now described, referring to FIGS. 5 to 7. FIG. 5 is a front view of the vacuum sampling tube 21; FIG. 6 is a longitudinal section view of the same; and FIG. 7 is a sectional view taken along the line VII—VII of FIG. 5 on magnified scale. The vacuum sampling tube 21 is a sampling vessel comprising a tubular casing 23 having a closed bottom and an opening at the other end and a cylinder 22 having openings at both ends as assembled in said casing 23 in the manner of a nest of boxes, and comprises the following structure. Thus,
1) the open top end 22a of the inner cylinder 22 of the nest of boxes is sealed gas-tight by a gas-barrier, needle-hole sealable plug 24,
2) said cylinder 22 is detachably associated, respectively, with the open end 23a of said tubular casing 23 in the vicinity of its open top end 22a in substantially liquid-tight relation and, with a plug means 23b of said casing 23 in the vicinity of its open bottom end 22b in substantially gas-tight relation,
3) said open bottom end 22b and said plug means 23 bare provided with complementary notches 22c and 23c and by bringing said cylinder 22 into sliding rotation about its axis, the internal spaces of said cylinder 22 and said casing 23 are reversibly brought into communication or out of communication,
4) a negative pressure state is kept within said cylinder 22; and
5) a specimen-pretreating reagent 25 is accommodated in a space between said cylinder 22 and said casing 23 surrounding the outside thereof.

The plug means 23b of said tubular casing 23 is a hollow cylindrical element erected from the bottom of said tubular casing 23 (the top surface of said cylindrical element is not closed) and its top end is acceptable with the outer peripheral surface of the open bottom end 22b of said cylinder 22. In this embodiment, said plug means 23b and said tubular casing 23 are provided as a one-piece molding.

The vicinity of the open end 22a and the vicinity of the open end 22b, as referred to above, are not necessarily the open end 22a and the open end 23b respectively, but may each be any location insofar the tubular casing 23 and cylinder 22 can be integrated to constitute a sampling tube 21 with the cylinder 22 held substantially liquid-tight and gas-tight before and during sampling.

Figure 8:
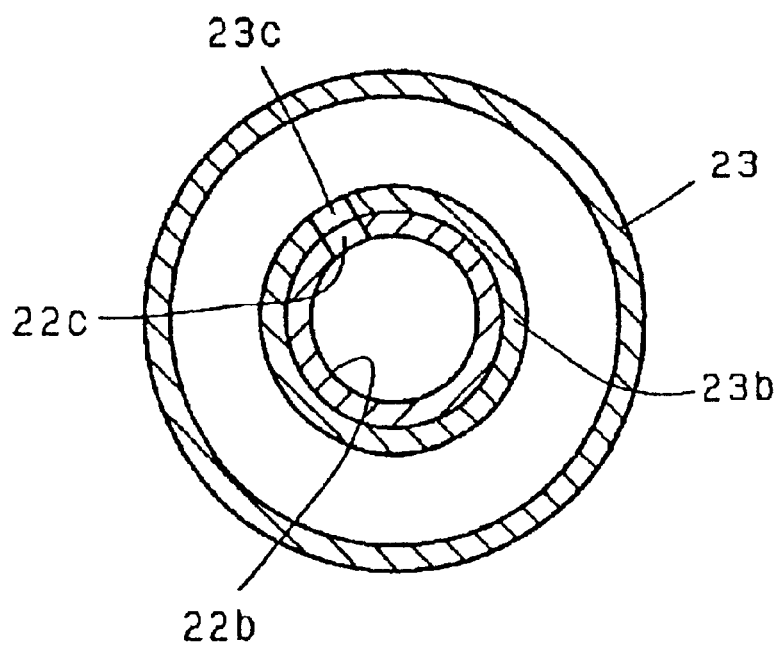
FIG. 8 is a sectional view showing a vacuum sampling tube according to the third aspect of the invention, with a notch of the open bottom end of the cylinder aligned with a notch of the plug means.

The seventh aspect of the invention is concerned with a vacuum sampling method which comprises using the vacuum sampling tube according to the third aspect of the invention, and collecting a specimen by vacuum into said cylinder 22 by the routine vacuum sampling method followed by, as illustrated in FIG. 8, bringing said cylinder 22 and said tubular casing 23 into relative rotation about the axis to substantially align the notch 22c of the open bottom end 22b of said cylinder 22 with the notch 23c of said plug means 23b, thereby bringing internal spaces of said cylinder 22 and said casing 23 into communication and introducing the specimen in said cylinder 22 into the pretreating reagent in said casing 23. Thereafter, both are blended and, assuming that the specimen is blood, it can be fractionated into blood corpuscles, serum and plasma by the routine method and used in various blood examinations.

Figure 9:
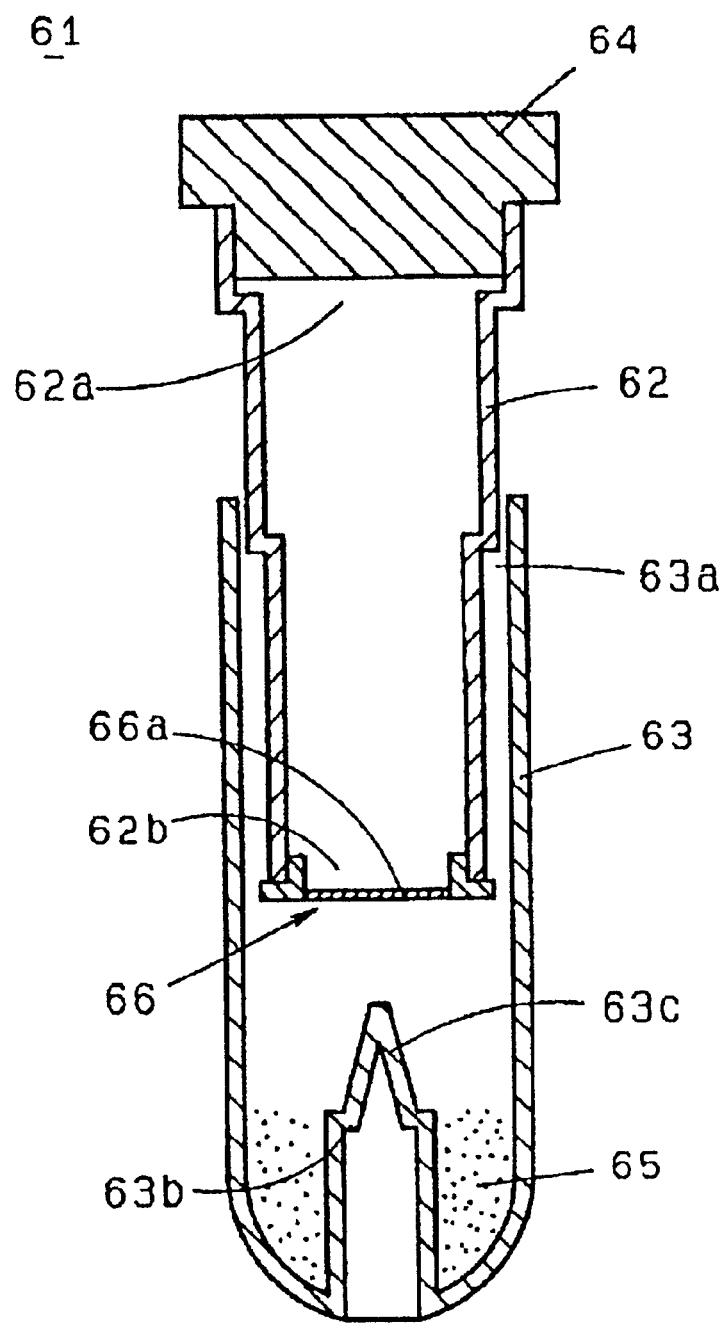
FIG. 9 is a sectional view showing an example of a vacuum sampling tube according to the fourth aspect of the invention.

An example of a vacuum sampling tube 61 of the fourth aspect of the invention is now described, referring to FIG. 9. The vacuum sampling tube 61 is a sampling vessel comprising a tubular casing 63 having a closed bottom and an opening at the other end and a cylinder 62 having openings at both ends as assembled in said casing in the manner of a nest of boxes, and comprises the following structure. Thus,
1) the open top end 62a of the inner cylinder 62 of the nest of boxes is sealed gas-tight by a gas-barrier, needle hole-sealable plug 64 while the open bottom end 62b thereof is sealed gas-tight by a gas-barrier member 66 which is in the form of a thin sheet and can be broken through at least locally, whereby a negative pressure state is kept within said cylinder 62,
2) said cylinder 62 is designed in such a manner that its open bottom end 62b faces a projected plunger member 63c disposed inwardly of the closed bottom end 63b of said tubular casing 63, and is detachably and slidably associated with the open end 63a of said tubular casing 63 in substantially liquid-tight relation in the vicinity of its open top end 62a, and
3) a specimen-pretreating reagent 65 is accommodated in a space between said cylinder 62 and said tubular casing 63.

In the illustrated embodiment, the gas-barrier member 66 which can be broken through at least locally is a plug-shaped element having a breakable part 66a consisting in a thin sheet fitted gas-tight to the open bottom end of said cylinder 62 but such barrier member 66 may of course be directly bonded or fused to the surface of said open end 62b by means of a hot-melt type, reaction-curable, or other adhesive or by the hitherto-known method such as ultrasonic or high-frequency heating. The area and shape of the breakable part 66a are not particularly restricted.

The vicinity of the open end 62a as referred to above is not necessarily the open end 62a but may be any location insofar as the tubular casing 63 and the cylinder 62 can be integrated to constitute a sampling tube 61 with the cylinder 62 held substantially liquid-tight before and during sampling.

Figure 10:
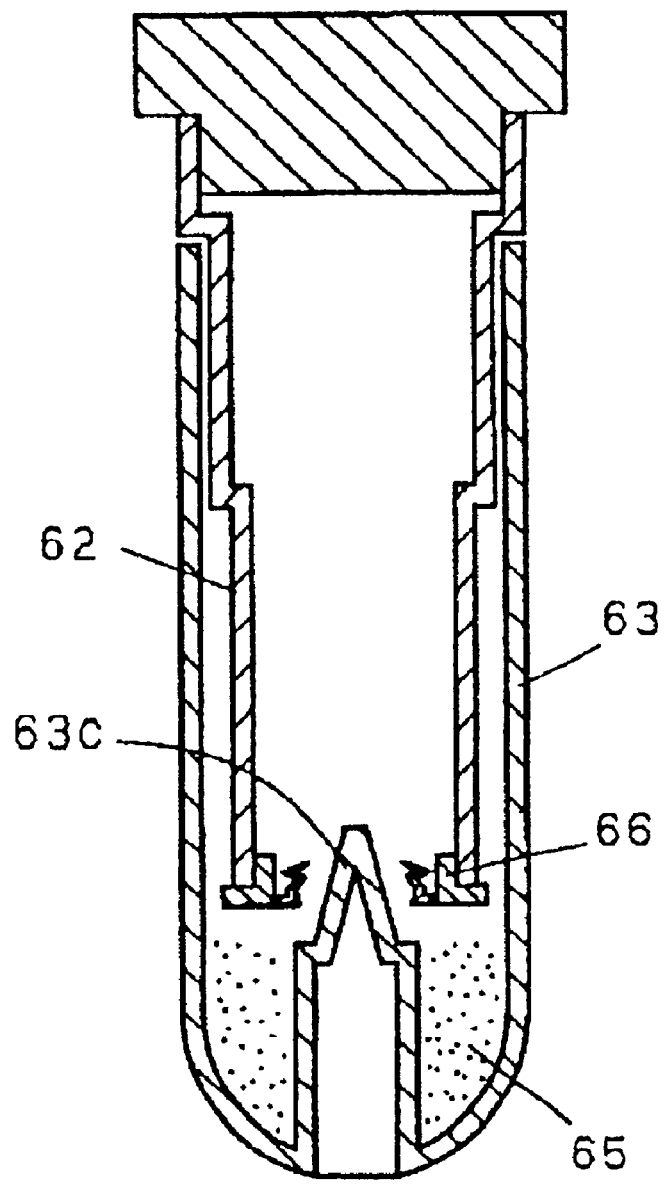
FIG. 10 is a sectional view showing the vacuum sampling tube according to the fourth aspect of the invention, with a plunger member having broken through a breakable gas-barrier member.

The eighth aspect of the invention is concerned with a vacuum sampling method which comprises using the vacuum sampling tube according to the fourth aspect of the invention, and collecting a specimen by vacuum into said cylinder 62 by the routine vacuum sampling method followed by, as illustrated in FIG. 10, causing said cylinder 62 and said tubular casing 63 to slide axially to break the gas-barrier member 66 which can be broken through at least locally, thereby introducing the specimen in said cylinder 62 into the pretreating reagent 65 in said tubular casing 63. Thereafter, both are blended and, assuming that the specimen is blood, it can be fractionated into blood corpuscles, serum, and plasma by the routine method and used in various blood examinations.

In the fourth aspect of the invention, the breakable part 66a of the gas-barrier member which can be broken through and the plunger member 63c are preferably offset from each other about the axis of said cylinder 62 and said tubular casing 63 prior to usage so that a sudden external force urging these members toward each other will not unintentionally bring said cylinder 62 into communication with said tubular casing 63.

Figure 11:
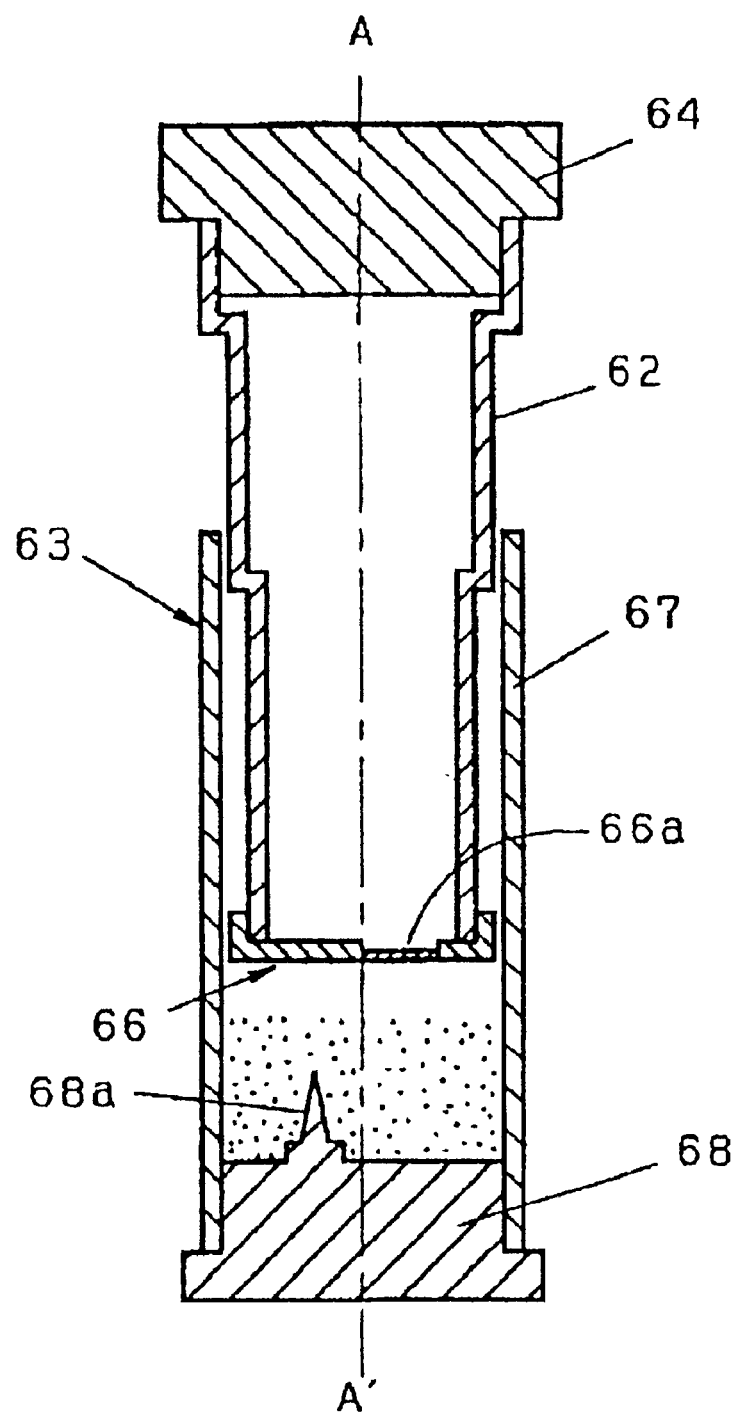
FIG. 11 is a sectional view showing another example of the vacuum sampling tube according to the fourth aspect of the invention.
Figure 12:
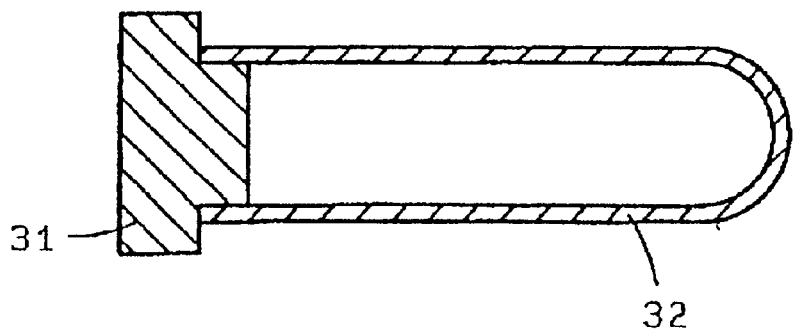
FIG. 12 is a sectional view showing the prior art vacuum blood collecting tube.
Figure 13:
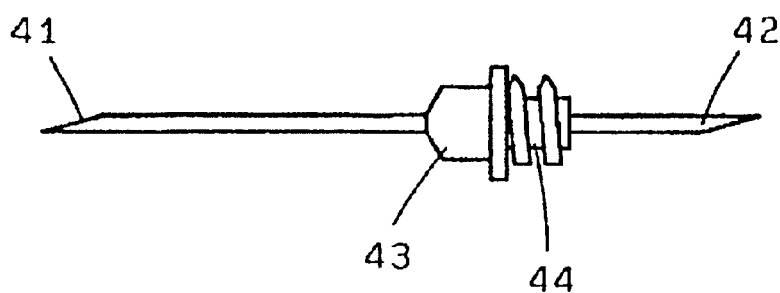
FIG. 13 is a sectional view showing a vacuum blood collecting needle.
Figure 14:
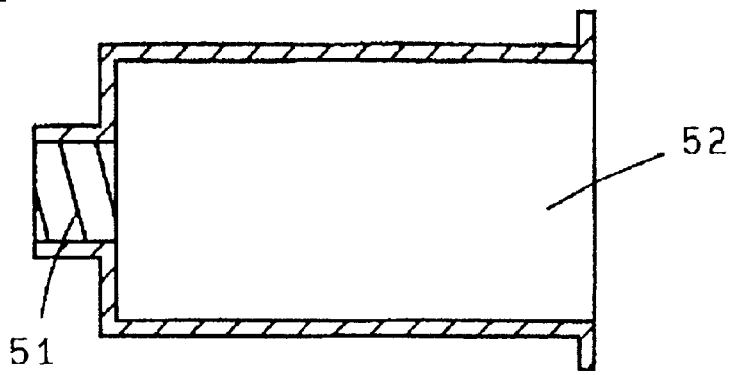
FIG. 14 is a sectional view showing a holder for vacuum blood collection.
Figure 15:
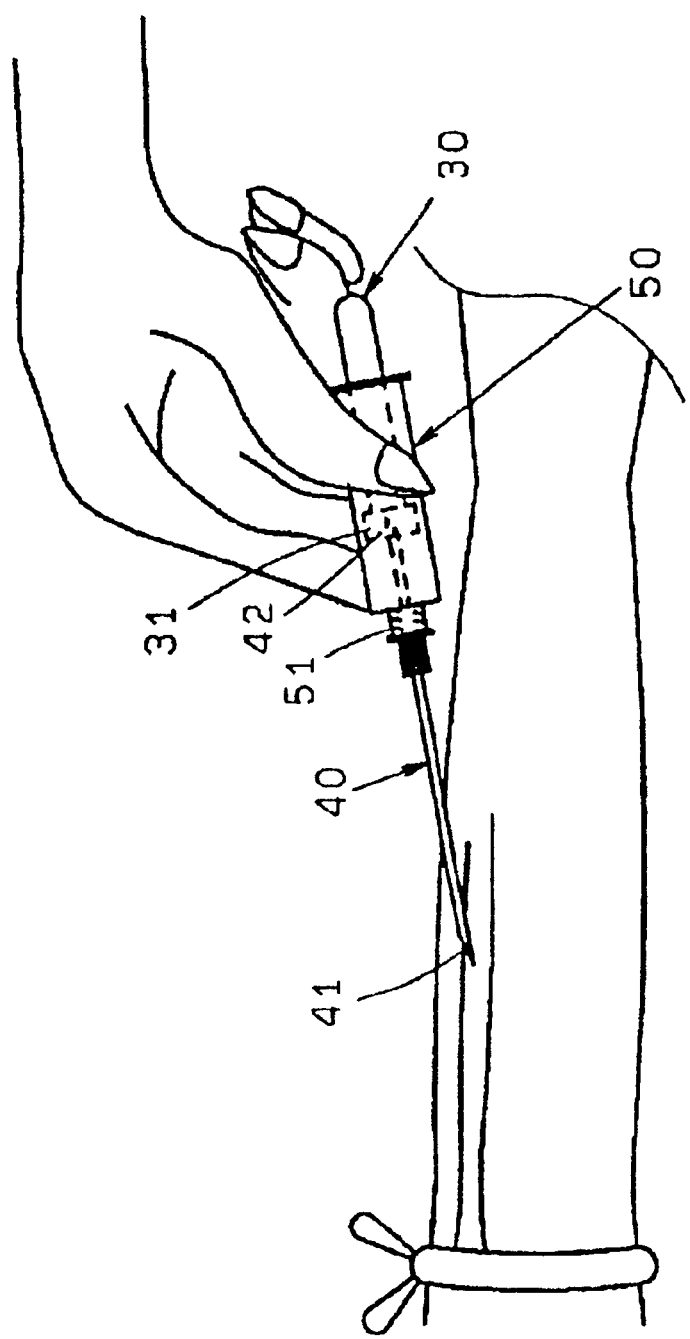
FIG. 15 is a sketch illustrating the vacuum blood collecting procedure using the prior art vacuum blood collecting tube.

FIG. 11 is a sectional view showing another example of the vacuum sampling tube 61 according to the fourth aspect of the invention. In this embodiment, the breakable part 66a of the gas-barrier member 66 which can be broken through and the plunger member 68a are offset from each other by 180 degrees.

Furthermore, in this embodiment, the tubular casing 63 is formed by fitting an independently molded plug element 68 having a plunger member 68a with a pre-molded cylindrical element 67. In such embodiment, after collection of a specimen, said cylinder 62 and said tubular casing 63 maybe brought into relative rotation about the A-A' axis to the location where both of said members can face each other and, then, be pushed against each other axially as described above.

In the first through fourth aspects of the present invention, as the material of the closed bottom casing and the cylinder having openings at both ends in the manner of a nest of boxes, for example, various kinds of glass such as hard glass, borosilicate glass, etc.; thermoplastic resins and thermoplastic elastomers obtainable by modification of synthetic or natural substances; thermosetting resins and crosslinkable elastomers; and metals can be used each independently or in combination, but transparent or translucent ones are preferred so that one may see through the inside.

The casing or cylinder assembled inside in the manner of a nest of boxes is necessary to be kept at a negative pressure state therein in order to carry out the vacuum sampling. Therefore, it is preferable to use materials having good gas-barrier properties. Thus, for example, glass and thermoplastic resins such as polyethylene terephthalate, polybutylene terephthalate, polyethylene naphthalate, polyacrylonitrile, polyamide, polyvinyl chloride, inclusive of their derivatives, the corresponding copolymers with other monomer components, and the corresponding compositions mixed with various additives are preferably used each independently or in combination.

As the material which is to constitute the gas-barrier member 66 which can be broken through according to the fourth aspect of the invention, the same materials as those mentioned above for the casing or cylinder assembled inside in the manner of the nest of boxes in which a negative pressure state is to be kept can be used. Addition to these, polyvinylidene chloride, ethylene-vinyl alcohol copolymer or an aluminum can be used each independently or in the form of thin laminate sheet derived therefrom.

In the first through fourth aspects of the invention, the vacuum sampling size can be selected by proper selection of the size of the casing or cylinder assembled inside in the manner of a nest of boxes and of the degree of decompression, etc.

The casing assembled outside in the manner of a nest of boxes is necessary to be detachably associated with, according to need, the casing or cylinder corresponding to the inner box in liquid-tight or gas-tight relation and, therefore, it is preferable to use a flexible material, for example, a thermoplastic resin or thermoplastic elastomer selected from among polyethylene, polypropylene, soft polyvinyl chloride, inclusive of their derivatives, the corresponding copolymers with other monomer components, and the corresponding compositions mixed with various additives. These may be used each independently or in a suitable combination by laminating, etc. In the case of olefin resins such as polyethylene and polypropylene, it is more preferable to use elastic materials obtainable by the copolymerization with an α-olefin monomer component using the so-called single-site catalyst. Of course, such flexible materials are not exclusive choices but even rigid materials can be utilized by inserting or laminating a packing material made of an elastic material between the fitting or sliding surface.

In the first through fourth aspects of the invention, as the material for the gas-barrier, needle-hole sealable plug to seal the casing or cylinder assembled inside in the manner of a nest of boxes gas-tight, for example, butyl rubber; a composite derived from an aluminum sheet and isoprene rubber or natural rubber; and a thermoplastic elastomer can be used appropriately.

When the plug is of a dismountable construction, by designing the inside diameter of the open end of the outer casing to be substantially equal to the inside diameter of the plug-accepting part of the casing or cylinder assembled inside in the manner of a nest of boxes, the inner casing or cylinder which is no longer necessary after the collected specimen has been blended with the pretreating reagent may be discarded and the plug may then be used as the plug for sealing the opening of the outer casing.

In the second and third aspects of the invention, the plug means of the outer casing which closes the open bottom end of the cylinder assembled inside in the manner of a nest of boxes gas-tight is molded integrally with the outer casing in the above-mentioned embodiments but it is possible to mold said plug means independently using butyl rubber or a thermoplastic elastomer and install it at the inner bottom surface of the outer casing or the inner wall surface of the cylinder in the vicinity of its open bottom end. Furthermore, the outer casing may also be molded as a cylindrical element in advance and, then, fitted with said pre-molded plug means to constitute the tubular casing.

In the first through fourth aspects of the invention, the specimen-pretreating reagent is the reagent to be blended with the specimen. For example, assuming that the specimen is blood, there may be mentioned at least one, or a combination, selected from among the known blood coagulation accelerator, anticoagulant, deproteinizing agent, hemolytic agent, and stabilizer for platelets and the like which are difficult to be stably maintained due to deactivation, denaturation, metabolism or evaporation, and an assay marker. These can be appropriately accommodated in the form of a solution, a granular powder or a lyophilizate or accommodated by coating on the wall surface or by supporting on beads, a sheet, a nonwoven fabric or the like.

In the above embodiments, the inner casing or cylinder does not contain any drugs that would possibly find its way into the body in the event of a backflow during sampling but may contain drugs already in use for various therapeutic purposes and of which safety has been confirmed, for example a heparin salt and so forth.

The casing assembled outside in the manner of a nest of boxes and the casing or cylinder assembled inside in the manner of a nest of boxes, which are to be used in the first to fourth aspects of the invention, can be manufactured by the known production method according to the respective materials to be used therefor. When the above material is a thermoplastic resin, for instance, the production method includes injection molding or blow molding. The vacuum sampling tube according to any of the first to fourth aspects of the invention can be manufactured by producing the casing assembled outside in the manner of a nest of boxes and the casing or cylinder assembled inside in the manner of a nest of boxes, etc. in the first place and fabricating them.

INDUSTRIAL APPLICABILITY

The conventional vacuum sampling system is available in a broad assortment of sampling tubes containing various pretreating reagents and each preset to a degree of decompression corresponding to each sample size. Therefore, taking the collection of blood as an example, all that is necessary for the person in charge of blood sampling is to pierce the blood vessel accurately with the blood collecting needle and to confirm that the blood flows in automatically due to the pressure difference between the blood vessel and the blood sampling tube. Thus, it is a laudable system contributory to labor saving and standardization of sampling. The only concern, however, is that the risk of the pretreating reagent which is contraindicated for injection finding its way into the body in the event of a backflow cannot be completely ruled out since the body and the blood collecting tube containing the pretreating reagent are brought into communication even at a short time.

However, with the vacuum sampling tube and in accordance with the vacuum sampling method of the invention, the space accommodating a specimen is completely isolated from the space accommodating the pretreating reagent at the time of vacuum sampling so that the risk of the pretreating reagent finding its way into the body in the event of a backflow is completely nil. It is, therefore, expected that the invention will expedite the spread of use of this sampling system with added safety.

In some examinations, it is necessary to follow up the time course of change in the reaction product resulting from the blending of the specimen with the pretreating reagent. In such cases, if the blending with the pretreating reagent begins immediately upon inflow of the specimen as it is the case with the prior art and if it takes much time before completion of blood collecting unexpectedly due to troubles such that the blood collecting needle does not remain properly secured in position because of the fineness of the subject's blood vessel or the subject's blood pressure drops during blood collecting, the reaction start time is obscured so that the proper monitor cannot be achieved. In this respect, as in the present invention, when the space accommodating a specimen is isolated from the space accommodating the pretreating reagent, both can be blended at one time immediately before carrying out an examination so that it is extremely useful to improve the accuracy of examinations.

What is claimed is:

1. A vacuum sampling tube which is a sampling vessel consisting of
    two tubular casings differing in size and each having a closed bottom and an opening at the other end as assembled together in the manner of a nest of boxes,
    in which
    1) the inner casing of the nest of boxes is sealed gas-tight at its open end by a gas-barrier, needle hole-sealable plug, whereby a negative pressure state is kept within said casing,
    2) the outer casing of the nest of boxes does not have a plug, and is substantially not in contact with an outer bottom surface of said inner casing of the nest of boxes but is detachably associated at the open end of said outer casing with an outer peripheral surface of said inner casing in the vicinity of its open end in substantially liquid-tight relation, and
    3) a specimen-pretreating reagent is accommodated in a space between said inner casing and said outer casing.

2. A vacuum sampling tube which is a sampling vessel consisting of
    a tubular casing having a closed bottom and an opening at the other end and
    a cylinder having openings at both ends as assembled in said casing in the manner of a nest of boxes,
    in which
    1) the open top end of the inner cylinder of the nest of boxes is sealed gas-tight by a gas-barrier, needle hole-sealable plug,
    2) said cylinder is detachably associated, respectively, with the open end of said tubular casing in the vicinity of its open top end in substantially liquid-tight relation and with a plug means of said tubular casing in the vicinity of its open bottom end in substantially gas-tight relation,
    3) a negative pressure state is kept within said cylinder, and
    4) a specimen-pretreating reagent is accommodated in the space between said cylinder and said tubular casing, and
    5) said tubular casing does not have a plug.

3. A vacuum sampling tube which is a sampling vessel consisting of
    a tubular casing having a closed bottom and an opening at the other end and a cylinder having openings at both ends as assembled in said casing in the manner of a nest of boxes,
    in which
    1) the open top end of the inner cylinder of the nest of boxes is sealed gas-tight by a gas-barrier, needle hole-sealable plug,
    2) said cylinder is detachably associated, respectively, with the open end of said tubular casing in the vicinity of its open top end in substantially liquid-tight relation and with a plug means of said tubular casing in the vicinity of its open bottom end in substantially gas-tight relation,
    3) said open bottom end and said plug means are provided with complementary notches and by bringing said cylinder into sliding rotation about its axis, internal spaces of said cylinder and said casing are reversibly brought into communication or out of communication,
    4) a negative pressure state is kept within said cylinder, and
    5) a specimen-pretreating reagent is accommodated in a space between said cylinder and said casing surrounding the outside thereof, and
    6) said tubular casing does not have a plug.

4. A vacuum sampling tube which is a sampling vessel consisting of
    a tubular casing having a closed bottom and an opening at the other end and a cylinder having openings at both ends as assembled in said casing in the manner of a nest of boxes,
    in which
    1) the open top end of the inner cylinder of the nest of boxes is sealed gas-tight by a gas-barrier, needle hole-sealable plug while the open bottom end thereof is sealed gas-tight by a gas-barrier member which may be broken through at least locally, whereby a negative pressure state is kept within said cylinder,
    2) said cylinder is designed in such manner that its open bottom end faces a plunger member disposed inwardly of the closed bottom end of said tubular casing and, is detachably and slidably associated with the open end of said tubular casing in substantially liquid-tight relation in the vicinity of its open top end, and
    3) a specimen-pretreating reagent is accommodated in a space between said cylinder and said tubular casing, and
    said tubular casing does not have a plug.

5. A vacuum sampling method
which comprises
  using the vacuum sampling tube according to claim 1 and collecting a specimen by vacuum into said inner casing
  followed by causing said inner casing to be dissociated from said outer casing, and
  adding the specimen in said inner casing to a pretreating reagent in said outer casing.

6. A vacuum sampling method
which comprises
  using the vacuum sampling tube according to claim 2 and collecting a specimen by vacuum into said cylinder
  followed by causing said cylinder and said tubular casing to slide axially to dissociate the open bottom end of said cylinder from said plug means,
  thereby introducing the specimen in said cylinder into a pretreating reagent in said tubular casing.

7. A vacuum sampling method
which comprises
  using the vacuum sampling tube according to claim 3 and collecting a specimen by vacuum into the cylinder
  followed by bringing said cylinder and said tubular casing into relative rotation about the axis to substantially align the notch of the open bottom end of said cylinder with the notch of said plug means,
  thereby bringing internal spaces of said cylinder and said casing into communication and
  introducing the specimen in said cylinder into a pretreating reagent in said casing.

8. A vacuum sampling method
which comprises
  using the vacuum sampling tube according to claim 4 and collecting a specimen by vacuum into said cylinder
  followed by pushing said cylinder into said tubular casing to break the breakable member at the bottom end of said cylinder by the plunger member of said tubular casing,
  thereby bringing both internal spaces of said cylinder and said casing into communication and
  introducing the specimen in said cylinder into a pretreating reagent in said casing.

* * * * *